United States Patent [19]

Brunengraber et al.

[11] Patent Number: 4,997,976
[45] Date of Patent: Mar. 5, 1991

[54] USE OF 1,3-BUTANEDIOL ACETOACETATE IN PARENTERAL ORAL NUTRITION

[76] Inventors: Henri Brunengraber, 730 Upper Roslyn Avenue, Westmount, Quebec, Canada, H3Y 1H9; Sylvain Desrochers, 5704 2e Avenue, Rosemont, Quebec, Canada, H1Y 2Y6; Bernard R. Landau, 19501 S. Woodland Rd., Shaker Heights, Ohio 44122

[21] Appl. No.: 271,613

[22] Filed: Nov. 15, 1988

[51] Int. Cl.$^5$ ............................................. C07C 69/66
[52] U.S. Cl. ..................................... 560/189; 560/174
[58] Field of Search ............................... 560/174, 189

[56] References Cited
PUBLICATIONS
CA 103(24):197467Y 1985.
CA 103(16): 132450b 1985.
CA 72(10): 45129b 1969.

Primary Examiner—Paul J. Killos
Attorney, Agent, or Firm—Eckert Seamans Cherin & Mellott

[57] ABSTRACT

Compositions for parenteral nutrition comprising a nutritionally effective amount of a compound of the following formula:

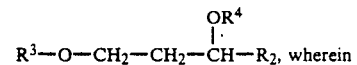

$R^2$ is methyl or ethyl, and
$R^3$ and $R^4$ are

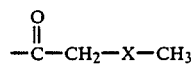

or H, and
X is —C=O or —HC—OH,
or a compound of the following formula:

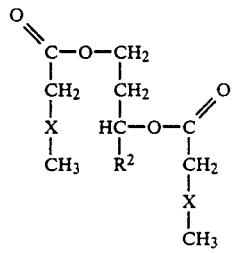

wherein
$R^2$ is methyl or ethyl, and
X is —C=O or —C—OH,
or mixtures thereof in association with a carrier.

2 Claims, No Drawings

USE OF 1,3-BUTANEDIOL ACETOACETATE IN PARENTERAL ORAL NUTRITION

BACKGROUND OF THE INVENTION

In recent years, parenteral nutrition has been widely practiced although its use is often accompanied by undesirable side effects such as infection, thrombosis, catheter and air embolization, and metabolic problems.

The use of parenteral nutrition has proved to be an extremely important tool in the treatment of a wide variety of diseases. For example, mortality form acute alimentary failure as in enterocutaneous fistula, has been considerably reduced by parenteral nutrition. Patients who have had extensive intestinal resection for such condition as Crohn's disease and ulcerative colitis have maintained good health at home for a long time on parenteral nutrition.

Parenteral nutrition also reduces the risks accompanying surgery in under-nourished patients, and promotes tissue repair and immune response following major surgery, trauma, and especially burns or multiple fractures with sepsis. Furthermore, short term parenteral nutrition has been lifesaving in comatose patients and in intractable anorexia nervosa. Support with parenteral nutrition has permitted chemotherapy and radiation therapy in patients with cancer otherwise considered unsuitable for any treatment.

However, even though parenteral nutrition has proved to be useful and necessary over the years, the concentrated fat emulsions that are used for the preparation of suitable solutions are mainly responsible for the various side effects that are encountered. Hence, the ideal source of calories of parenteral nutrition should have a high caloric density, a total solubility of water, no ionic charge, thus avoiding the necessity of administering a counter ion lid $Na^+$, good diffusibility through cell membranes to avoid hyperosmolality, rapid metabolism to acetyl-CoA and protein sparing action.

There are good reasons to believe that 1,3-butanediol, either as a DL mixture or as the L-isomer can meet most of the above-mentioned criteria. The DL mixture has ben investigated as a component of animal feed for a long time. When humans were fed a diet containing 5% of DL-1,3-butanediol, nitrogen was spared and there was no adverse effect. Furthermore, DL-1,3-butanediol alleviates the ethanol withdrawal syndrom in rats thus making it a potential therapeutic agent in human alcoholics. DL-1,3-butanediol is metabolised in the liver to DL-3-hydroxybutyrate via alcohol and aldehyde dehydrogenase; the D-$\beta$-hydroxybutyrate is an oxydo-reduction equilibrium with acetoacetate via the action of D-$\beta$-hydroxybutyrate dehydrogenase.

On the other hand, L-$\beta$-hydroxybutyrate is not a natural compound although it is very well used by mammalian cells. In addition, it has been demonstrated that L-1,3-butanediol is useful in reducing the blood glucose level of streptozotocin-diabetic rats.

However, although the use of butanediol in parenteral nutrition and diabetic control looks promising, the use of this substance presents some drawbacks. First, butanediol has a low molecular weight. As a result from this, high amounts of butanediol must be employed in order to provide sufficient calory intake. Furthermore, butanediol is a strong reducing agent and there is a possibility of creating an oxidation-reduction imbalance if parenteral nutrition is to be maintained for a long period of time.

Therefore, a parenteral composition comprising a compound replacing the usually employed concentrated fat emulsion and having a high molecular weight, a proper oxidation-reduction balance as well as minimal side effects would be highly desirable.

SUMMARY OF THE INVENTION

In accordance with the present invention, there is provided novel compounds to be used in enteral or parenteral compositions. These compounds have the following general formula I:

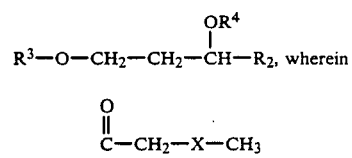

$R^2$ is methyl or ethyl, and
X is —C=O or —HC—OH.
in association with a pharmaceutically acceptable carrier.

The corresponding reduced 3-hydroxybutyrate derivatives of the above-mentioned compound also fall within the scope of the present invention.

There is also provided a composition to be used for enteral or parenteral nutrition and comprising a butanediol-bis-acetoacetate having the following general formula II:

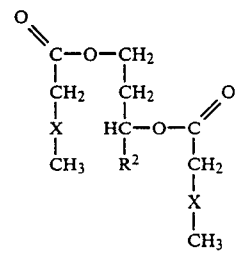

wherein
$R^2$ is methyl or ethyl, and
X is —C=O or —C—OH.
in association with pharmaceutically acceptable carrier.

Also within the scope of the present invention is a composition to be used for enteral or parenteral nutrition, said composition comprising the above-mentioned novel butanediol-acetoacetate compounds or butanediol-bis-acetoacetates or mixtures thereof in association with a suitable carrier.

It is also an object of the present invention to provide a method for the nutritional support of a patient receiving otherwise inadequate nutrition, said method consisting in parenterally administering a composition comprising the above-mentioned novel compounds or butanediol-bis-acetoacetate or mixtures thereof in association with a suitable pharmaceutically carrier.

DETAILED DESCRIPTION OF THE INVENTION

The present invention relates to butanediol-acetoacetate compounds and derivatives thereof having the following general Formula I:

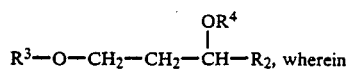

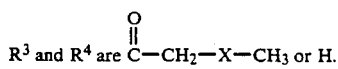

$R^2$ is methyl or ethyl, and
X is —C=O or —HC—OH.

These compounds are hereinafter generally referred to as butanediol-acetoacetate. The term butanediol-acetoacetate is meant to include all the compounds and functional derivatives thereof represented by formula I.

The present invention is also concerned with a new use in enteral or parenteral nutrition of the known butanediol-bis-acetoacetates having the following Formula II:

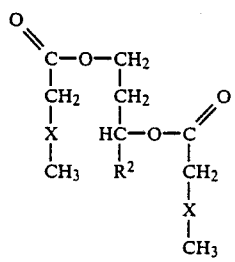

wherein
$R^2$ is methyl or ethyl, and
X is —C=O or —C—OH.

These compounds are hereinafter generally referred to as butanediol-bis-acetoacetate. The term butanediol-bis-acetoacetate is meant to include all the compounds and functional derivatives thereof represented by Formula II.

The compounds described herein contain one or more center of asymmetry and may thus give rise to diastereoisomers and optical isomers. The present invention is meant to include such possible diastereoisomers as well as their recemic and resolved, optically active forms.

Generally speaking, when reference is made to the butanediol-acetoacetate compounds of the present invention, it refers to their racemic mixtures containing both the D and L forms. However, there is an interest at producing the corresponding reduced 3-hydroxybutyrate derivatives, in particular DL-1,3-butanediol-DL-$\beta$-hydroxybutyrate and L-1,3-butanediol-L-$\beta$-hydroxybutyrate. The latter is particularly useful s an antidiabetic agent since its metabolism generates two molecules of L-$\beta$-hydroxybutyrate which, as mentioned earlier, has demonstrated interesting antidiabetic properties.

Other preferred compounds that fall within the scope of the present invention are those of Formula 1 found int h form of a mixture comprising the compounds wherein $R^4$ is hydrogen, $R^2$ is methyl and $R^3$ is  (a)

$R^3$ is hydrogen, $R^2$ is methyl and $R^4$ is 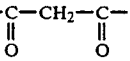 (b)

Also, when reference is made to the butanediol-bis-acetoacetate compounds and derivatives thereof to be used in the context of the present invention, it refers to their racemic mixtures containing both D and L forms.

UTILITY

The compounds of Formula I and II are useful as total or partial replacement of the concentrated fat emulsions that are used for intravenous parenteral nutrition. These compounds may also be included in infant nutrition formulas given to children suffering from various defects in $\beta$-oxidation of fatty acids, such as deficiencies in acyl-CoA dehydrogenase, hydroxymethyl-glutaryl-CoA lyase or carnitine, thereby alleviating some cases of the sudden infant death syndrom (SIDS) by which some newborns die of hypoglycemia related to impaired fatty acid oxidation.

Furthermore, during the sucking period and the following weeks, the brain of newborn mammals preferentially uses ketone bodies to synthesize large quantities of lipids which are used in the process of myelinization of neurons. Therefore, ingestion of butanediol-acetoacetate or butanediol-bis-acetoacetate compounds by children at risk for SIDS would not only spare the reserves of liver glycogen but also supply a fuel preferentially used by the developing brain.

The compounds of the present invention may also replace medium-chain triglycerides in the treatment of patients suffering from fat malabsorption. Furthermore, under hypermetabolic conditions such as trauma, infection or large burns, ketone body concentration in blood are very low. This is explained by the hypermetabolic state of the liver whose ATP requirements are greatly increased for the synthesis of shock proteins. Thus, fatty acid carbon is completely oxidized via the Krebs cycle, while little is spilled out as ketone bodies. Thus, in hypermetabolic states, the liver does not provide ketone bodies (a soluble form of fat) to peripheral tissues. Since ketone bodies are well used by peripheral tissues as a source of energy, they could be supplied in the form of butanediol-acetoacetate to patients either orally or via a stomach tube.

A further use of the compounds of the present invention resides in the replacement of glucose in peritoneal dialysis solutions. These solutions often contained high concentrations of glucose to prevent absorption of the solution's water and to remove the excess water from the patient. Unfortunately, this usually leads to undesirable hyperglycemia, especially in diabetic patients. Butanediol-acetoacetate or butanediol-bis-acetoacetate or mixtures thereof used instead of glucose do not lead to hyperglycemia and supply an easily metabolisable fuel.

Also, the novel butanediol mono- and diacetoacetate could advantageously replace the ketogenic diet in the treatment of children suffering from either intractable epileptic seizures which cannot be controlled by medication or form inborn errors of metabolism, such as deficiency in pyruvate dehydrogenase accompanied or not by psychological and intellectual problems (certain forms of autism or Rett's disease).

When these children are treated with ketogenic high fat diet, there is poor compliance because of the unsalability of the diet. In addition, any intake of carbohydrates can lead to either seizures or deterioration of the condition of the child since carbohydrates inhibit conversion of the fat in the ketogenic diet to ketone bodies. In contrast, the ketogenic potential of the compounds of the present invention, especially butanediol mono- and diacetoacetate, is not affected by the presence of carbohydrate in the diet. Thus, it is likely that these children could be kept on an normal diet with addition of 5 to 10% of the daily caloric requirement as butanediol esters dissolved in fruit or vegetable juice or in chocolate drink.

Furthermore, when massively obese people are treated with total or almost total caloric restriction in a metabolic ward, it takes a few days for ketosis to develop in the patient. Once ketosis is developed , its appetite inhibiting effect helps the patient comply with the treatment. However, during the first few days of the treatment, when ketosis is still low, it si difficult and stressful for the patient to comply with the restrictions. It is hypothesized that ketosis could be rapidly induced during severe caloric restriction by giving the patient an appropriate amount of the novel butanediol esters of the present invention in divided doses over the first day. This would prime the ketotic stat of the patient and allow him or her to adjust easily to the treatment.

It has also been noted that the use of the mono-and diesters of acetoacetate and butanediol described herein have the following advantages over the use of butanediol alone:

(a) the metabolism of the esters in the liver after hydrolysis in plasma leads to mixtures of 3-hydroxybutyrate and acetoacetate which are in a physiological oxido-reduction ratio. In contrast, using butanediol alone leads to a mixture of 3-hydroxybutyrate and acetoacetate which is more reduced than physiological. Thus, the butanediol esters of acetoacetate could be included in general parenteral solutions as precursors of 3-hydroxybutyrate and acetoacetate and as oxido-reduction buffers as recommended by R.L. Veech (Am. J. Clin. Nut.,44:519–51, 1986).

(b) the use of the esters of butanediol leads to a lower butanediol concentration in plasma thus alleviating any potential effect of this alcohol on the brain.

(c) when butanediol derived from hydrolysis of its acetoacetate esters is oxidized in the liver to 3-hydroxybutyrate, the bulk of the reducing equivalents (NADH) generated by butanediol oxidation is trapped in acetoacetate and exported from the liver as 3-hydroxybutyrate. Thus there is no oxido-reduction shift in the liver towards the more reduced state which could, under certain circumstances, inhibit gluconeogenesis (synthesis of new glucose molecules) and lead to hypoglycemia.

Finally, butanediol-acetoacetate and butanediol-bis-acetoacetate can be used as a component of animal feed since ketone bodies are preferentially used by lactating mammary glands and the developing brain. For example, it could be used as a food supplement in the mash of sows during the last third of pregnancy and in the lactating period. It can also be used for bottle-feeding of new born pigs too weak to compete for their mother's nipple and it can be used the mash of newborn chicken.

CONCENTRATION IN PARENTERAL SOLUTIONS.

The concentration of the novel butanediol-acetoacetate of the present invention o be used for parenteral administration will depend on various factors but will generally range between 5 and 100% wt/vol. This concentration may be that which is intended of use, e.g. about form 5 to 20% wt/vol., or may be more concentrated, e.g. about from 25 to 100% wt/vol. or the limit saturated concentration of the compound.

As for the butanediol-bis-acetoacetate, its concentration in parenteral solutions will generally range between 5 and 100% wt/vol. Again, the concentration may be that which is intended for use, e.g. about from 5 to 15% wt/vol., or may be more concentrated, e.g. 10 to 100% wt/vol. in the case of saturated solutions. When it is intended to use a mixture of butanediol-acetoacetate and butanediol-bis-acetoacetate, the proportions of each compound will generally range between 1:4 and 4:1% wt/vol., with concentration values ranging from 5 to 20% wt/vol. for ready to use solutions and from 5 to 100% wt/vol. for concentrated stock solutions.

Concentrated solutions are maintained at a greater concentration to enhance the compounds stability during autoclaving or storage. Such solutions are then diluted to the desired administration concentration at some convenient point before use. If necessary, the butanediol-acetoacetate or butanediol-bis-acetoacetate or mixtures thereof need not be incorporated in an aqueous solution at all until reconstitution before administration. This, however, is not a commercially desirable as supplying a ready-to-use solution.

The solutions of butanediol-acetoacetate or butanediol-bis-acetoacetate or mixtures thereof frequently will be mixed with other nutrients or with drugs. Such other nutrients may include nitrogen sources such as aminoacids, vitamins, minerals, and electrolytes including trace elements. Other calory sources such as carbohydrates or lipids may not be needed but may also be maintained in the solution. The aminoacids are mixed with the butanediol-acetoacetate or butanediol-bis-acetoacetate or mixtures thereof prior to or after sterilization. A mixture of essential aminoacids nutritionally balanced will ordinarily be sufficient, although no essential aminoacids may be included. The proportions may be adjusted for special disease states, e.g., inborn errors of metabolism, in accord with known practice.

PACKAGING OF PARENTERAL SOLUTIONS

The solution are packaged in conventional parenteral solution containers, either glass or thermoplastic flexible bags. Such containers are sterile, sealed and will contain means for communicating with the patient's circulation, either alone or in concert with other devices. Typically, the means for communicating with the pateint's circulation will be a frangible member associated with a container which is adapted to enter into fluid communications with an administration set. Such sets are also well known.

ADMINISTRATION AND DOSAGE

The solutions usually are parenterally administered by infusion into a peripheral vein although they may also be infused through a central veinous catheter. The solutions are infused at a rate sufficient to maintain the nutritional status of the patient in concert with the intake of other nutrients. Infusion will be ordinarily about form 1 to 7 Kcal/dg patient weight/day for an adult patient and from 1 to 30 Kcal/kg patient weight/day for a pediatric patient but the amount administered parenterally will depend upon the patient's oral intake of butanediol-acetoacetate or butanediol-bis-acetoacetate or mixtures thereof or orther nutrients as well as the patient's metabolic needs.

The butanediol-acetoacetate or butanediol-bis-acetoacetate or mixtures thereof of the present invention can be taken orally, and they have the advantage of a higher energy content than glucose so are less likely to cause diarrhea or other intestinal distress at a given Kcal dose when compared to glucose. The novel compounds of the present invention, either alone or in combination with other nutrients as described above or with drugs, can be taken by gastric tube or as a component of ordinary meals. Since these compounds are to function as nutrients, they are supplied in quantities sufficiently high to provide greater than 15% preferably greater than 25% of the calories required by the patient.

PREPARATION OF BUTANEDIOL-ACETOACETATE AND BUTANEDIOL-BIS-ACETOACETATE

The novel butanediol-acetoacetate compounds of the present invention are generally prepared by reacting, in the presence of a catalyst, equimolar amounts of diketene and a suitable diol. The catalysts which may be used in the context of the present invention are selected from anhydrous sodium acetate or any suitable acid catalyst while the diol may be selected from 1,3-butanediol, 1,3-pentanediol and the like. The temperature at which the reaction is to be performed may vary from 25° to 120° C. Following the complete addition of the diketene, the solution is then purified by distillation and column chromatography. The distillation temperature will vary from 0° to 120° C. depending on both the nature of the substituants and the pressure. Furthermore, a column of silicon dioxide eluted with a mixture of ethyl acetate; methylene chloride is preferred for chromatography purification.

Alternatively, purification can be conducted through filtration on flash silica and elution with a mixture of hexane-ethylacetate. Also it is possible to purify the compounds of the present invention through dissolution in water and treatment with a mixture of anion- and cation-exchange resins. The discolorized and neutral solution is then extracted with chloroform. the extract is dried on sodium sulfate, filtered and evaporated under vacuum.

The butanediol-bis-acetoacetates are known compounds and their preparation is described in Beilsteins Baud III, II 3,659.

The present invention is further defined by reference to the following examples which are intended to be illustrative and not limiting.

EXAMPLE 1

Preparation of 1,3-butanediol-acetoacetate

Five mmol of anhydrous sodium acetate are suspended in 1 mol of 1,3-butanediol which is heated under stirring to 55° C. 1.1 mol of diketene is added drop by drop over a period of 1.5 hours. The rate of diketene addition is such that temperature of the reaction mixture remains between 55° and 60° C. When addition of diketene is completed, the temperature is allowed to drop to about 40° C., where it is kept for about 1 hour. Then the reaction mixture is distilled under vacuum. After a first fraction containing unreacted 1,3-butanediol, the monoesters distil at 100° C. under 0.05 mm Hg. The diester distils at 109° C. under 0.05 mmg Hg. Further purification of the monoester and the diester is achieved using a column of silicon dioxide eluted with a mixture of ethyl acetate; methylene chloride (60:40). On this column, the order of elution is: the diester, the monoester and a trace of unreacted butanediol. The mono and diester purified by this procedure were used to obtain the infrared and NMR spectra.

A mixture of acetoacetic acid, 3-hydroxybutyl ester (A) and acetoacetic acid, 1-methyl 3-hydroxypropyl ester (B) is obtained.

| MOLECULAR WEIGHT | 174.20 |
| REFRACTIVE INDEX | $1.4462^{25}$ |
| BOILING POINT (°C.) | $100^{\circ .05mm}$ |
| COMPOUND A/COMPOUND B | 3.043 |

| PROTON NMR SPECTRUM ASSIGNMENTS (ppm) | |
| --- | --- |
| A  1.23,d,3H,CH$_3$ | G  3.67,t,2H,CH$_2$ |
| B  1.30,d,3H,CH$_3$ | H  4.26,t,2H,CH$_2$ |
| C  1.80,m,4H,CH$_2$ | I  4.28,m,1H,CH |
| D  1.96,s,6H,CH$_3$ | J  4.96,s,1H,CH |
| E  2.27,s,6H,CH$_3$ | K  6.17,m,1H,CH |
| F  3.47,s,4H,CH$_2$ | SOLVENT: CDCl$_3$ |
| | REFERENCE TMS |

| CARBON-13 NRM SPECTRUM ASSIGNMENTS (ppm) | | | | | |
| --- | --- | --- | --- | --- | --- |
| A | 20.1 | B | 21.1 | C | 23.5 |
| D | 30.1 | E | 37.7 | F | 38.0 |
| G | 38.7 | H | 49.9 | I | 50.3 |
| J | 58.5 | K | 61.2 | L | 62.7 |
| M | 64.5 | N | 69.7 | O | CDCl$_3$ |
| P | 89.6 | Q | 90.3 | R | 167.1 |
| S | 167.3 | T | 200.9 | U | UNOBSERVED |
| | | | | SOLVENT CDCl$_3$ | |
| | | | | REFERENCE TMS | |

EXAMPLE 2

Alternate process for the preparation of 1,3-butanediol-acetoacetate.

5 mmol of triethylamine are mixed with 1 mol of 1,3-butanediol. The mixture is kept on ice and stirred while 1 mol of diketene is added dropwise over 1.5 hours. Stirring is continued for 5 to 7 hours at 0° C., then for 15 hours at room temperature. The reaction is monitored occasionally by proton NMR and after 15 hours, it is complete. This procedure yields a mixture of butanediol-acetoacetate and butanediol-diacetoacetate in proportion 77:23 (assayed by gas chromatography). Butanediol-diacetoacetate can be obtained as a main product by reacting 1 mol of butanediol with 2 mol of diketene.

Purification of product of synthesis can be conducted by either;

(a) filtration on flash silica and elution with a mixture of hexane-ethylacetate 60:40 yields a mixture of mono- and diester. Yield 84%.

(b) dissolution in water and treatment with a mixture of anion- and cation-exchange resins. The discolorized and neutral solution is extracted with chloroform. The extract is dried on sodium sulfate, filtered and evaporated under vacuum. Yield of synthesis is 85%.

The physical characteristics of the product obtained are given in Example 1.

What is claimed is:
1. DL-1,3-butanediol-DL-$\beta$-hydroxybutyrate.
2. L-1,3-butanediol-L-$\beta$-hydroxybutyrate.

* * * * *